(12) United States Patent
Corriu et al.

(10) Patent No.: US 6,524,372 B1
(45) Date of Patent: Feb. 25, 2003

(54) SILICA GEL INCORPORATING POLYAZACYCLOALKANE STRUCTURAL UNITS

(75) Inventors: Robert Corriu, Montpellier (FR); Catherine Reye, Montpellier (FR); Ahmad Mehdi, Montpellier (FR); Gérard Dubois, Montpellier (FR); Claude Chuit, Junas (FR); Franck Denat, Dijon (FR); Bruno Roux-Fouillet, Dijon (FR); Roger Guilard, Fontaine les Dijon (FR); Gilles Lagrange, Forges les Bains (FR); Stéphane Brandes, Dijon (FR)

(73) Assignee: L'Air Liquide, Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 09/600,954

(22) PCT Filed: Jan. 25, 1999

(86) PCT No.: PCT/FR99/00142

§ 371 (c)(1),
(2), (4) Date: Jul. 25, 2000

(87) PCT Pub. No.: WO99/37656

PCT Pub. Date: Jul. 29, 1999

(30) Foreign Application Priority Data

Jan. 26, 1998 (FR) .............................. 98/00785

(51) Int. Cl.[7] .................. B01D 53/02; B01J 20/22; C01B 13/08; C01B 15/013; C07D 257/08
(52) U.S. Cl. .................. 95/138; 210/687; 423/219; 423/239.1; 423/584; 502/405; 502/407; 516/101; 540/474
(58) Field of Search .................. 540/474; 516/101; 95/138; 423/239.1, 584, 219; 210/687; 502/405, 407

(56) References Cited

U.S. PATENT DOCUMENTS

| | | | | |
|---|---|---|---|---|
| 3,860,576 A | * | 1/1975 | Ham et al. | 540/474 |
| 5,120,443 A | * | 6/1992 | Bruening et al. | 210/638 |
| 5,188,816 A | * | 2/1993 | Sherry et al. | 540/474 X |
| 5,428,156 A | * | 6/1995 | Mease et al. | 540/474 |
| 5,489,425 A | * | 2/1996 | Kruper, Jr. et al. | 540/474 X |
| 5,891,574 A | * | 4/1999 | Guilard et al. | 428/404 |
| 6,139,603 A | * | 10/2000 | Boisselier-Cocolios et al. | 95/138 X |
| 6,265,483 B1 | * | 7/2001 | Guilard et al. | 428/404 X |
| 6,372,903 B1 | * | 4/2002 | Mehdi et al. | 540/474 |

OTHER PUBLICATIONS

Battioni et al.: Metalloporphrinosilicas: A New Class of Hybrid Organic–Inorganic Materials Acting as Selective Biomimetic Oxidation Catalysts, *Chem. Commun.*, 1996, 2037–2038.*

Dudler et al.: An Oxygen–Nitrogen Donor Macrocycle Immobilized on Silica Gel. A Reagent Showing High Selectivity for Copper (II) in the Presence of Cobalt (II), Nickel (II), Zinc (II) or Cadmium (II), Aust. J. Chem., 1987, 40, 1557–63.*

Luitjes, Hendrikus et al: "Reactions of the Butyl Lithiums with Tertiary Oligoethylene Polyamines", Tetrahedron (1997), 53(29), 9977–9988.*

Gros, C. et al: "New Silica–Gel–Bound Polyazacycloalkanes and Characterization of their Copper (II) Complexes Using Electron Spin Resonance Spectroscopy", J. of the Chemical Society, Dalton Transactions, 1996, pp. 1209–1214.*

* cited by examiner

*Primary Examiner*—Richard D. Lovering
(74) *Attorney, Agent, or Firm*—Young & Thompson

(57) ABSTRACT

A novel compound which can be used in the field of separation and purification of gases is disclosed. The compound can be incorporated into a silica gel incorporating polyazacycloalkane structural units for separating a predetermined gas from a mixture of gases. The mixture of gases is brought into contact with a metallated hybrid gel under conditions which make possible the absorption of the gas to be separated, followed by a phase of desorption of the attached gas, and the recovery of the gas.

18 Claims, No Drawings

SILICA GEL INCORPORATING POLYAZACYCLOALKANE STRUCTURAL UNITS

This application is a 371 of PCT/FR 99/00142 filed Jan. 25, 1999.

A novel material which can be used in the field of the separation and purification of gases is disclosed. Current separation techniques, whether cryogenic distillation or adsorption on zeolites, and techniques for the purification of industrial gases by cryogenic or catalytic distillation are not always capable of being optimized, either in economic terms or in terms of purity. Many studies have furthermore shown that gases such as oxygen, hydrogen or carbon monoxide react selectively and reversibly with transition metal complexes.

BACKGROUND OF THE INVENTION

Thus, cobalt(II) complexes of cyclam or of cyclene easily fix atmospheric oxygen (Machida R., Kimura E., Kodama M., *Inorg. Chem.*, 1983, 22, 2055–2061) and result in $\mu$-peroxide species in aqueous media. However, the lifetime of the oxygen-comprising complexes in solution is limited as the latter can undergo irreversible decomposition reactions (Martell A. E., Basak A. K., Raleigh. C. J., *Pure Appl. Chem.*, 1988, 60, 1325–1329). Furthermore, these species cannot be deoxygenated simply by decreasing the dioxygen partial pressure. An improvement in the reversibility, necessary in a separation process, requires stabilization of the intermediate superoxide species. Grafting the ligand to a solid matrix should, at the same time, slow down the change from the superoxide species to the $\mu$-peroxide species, restrict hydrolysis reactions and facilitate the handling of the active complex (Tsuchida E., Nishide, H. *Top. Curr. Chem.*, 1986, 32, 63–99). The incorporation of cobalt complexes with porphyrins, phthalocyanines or cyclidenes in organic or inorganic polymers, such as silica gels, and the study of the interaction of these materials with oxygen have already formed the subject of numerous studies. Generally, the complex is synthesized in a first stage and then immobilized on the polymer via a dative bond between a nitrogen atom of a pyridine or imidazole unit and the metal (Nishide H., Suzuki T., Kawakami H., Tsuchida E., *J. Phys. Chem.*, 1994, 98, 5084–5088; Cameron J. H., Graham S., *J. Chem. Soc. Dalton Trans.*, 1992, 385–391; Bowman R. G., Basolo F., Burwell Jr. R. L., *J. Am. Chem. Soc.*, 1975, 97, 5125–5129). Another approach consists in attaching, in a first step, the ligand to the polymer via a covalent bond and in subsequently metallating (Wöhrle D., Gitzel J., Krawczyk G., Tsuchida E., Ohno H., Okura I., Nishisaka T., *J. Macromol. Sci. Chem.*, 1988, A25, 1227–1254; Barnes M. J., Drago R. S., Balkus Jr. K. J., *J. Am. Chem. Soc.*, 1988, 110, 6780–6785). Thus, the grafting to silica gel of tetraazamacrocyclic ligands and the study of the metallation of these materials have been carried out (Gros C., Rabiet F., Denat F., Brandes S., Chollet H., Guilard R., *J. Chem. Soc. Dalton Trans.*, 1996, 1209–1214). The sol-gel process has been studied in detail (Hench L. L., West J. K., *Chem. Rev.*, 1990, 90, 33–72) and is of major importance in the chemistry of the materials. One of the main advantages of this process is a high homogeneity of the materials obtained, thus conferring specific properties on them. Precursors of alkoxide type are among the most widely used. Thus, the hydrolysis of tetraethoxysilane in solution in an organic solvent, for example an alcohol, results in a colloidal dispersion of particles, which particles result from the polymerization of the precursor and which dispersion is referred to as a sol. This sol changes in the direction of the formation of a gel. The drying of this gel by evaporation results in a xerogel, which can itself be converted into glass or ceramic. More recently, this technique has made possible the preparation of novel organic-inorganic hybrid materials (Corriu R. J. P., Leclercq D., *Angew. Chem. Int. Ed.*, 1996, 35, 1420–1436; Schubert U., Hüsing N., Lorenz A., *Chem. Mater.*, 1995, 7, 2010–2027). The precursor is then an organic compound carrying one or more endings of trialkoxysilyl [$Si(OR_3)$] or silyl [$SiH_3$] type. Various organic species have been used, such as aromatic compounds, acetylenic units or linear and cyclic amines (Corriu R. J. P., Leclercq D., *Angew. Chem. Int. Ed.*, 1996, 35, 1420–1436; Khatib I. S., Parish R. V., *J. Organomet. Chem.*, 1989, 369, 9–16; Tsuda T., Fujiwara T., *J. Chem. Soc. Chem. Commun.*, 1992, 1659–1661). Battioni et al. have used this route to incorporate manganese and iron porphyrins in a silica gel and have tested the catalytic properties of these novel materials (Battioni P., Cardin E., Louloudi M., Schöllhorn B., Spyroulias G. A., Mansuy D., Traylor T. G., *Chem. Commun.*, 1996, 2037–2038).

SUMMARY OF THE INVENTION

The anchoring of a complex to a polymer via a dative bond between a base and the metal exhibits the advantage of activating the complex and of stabilizing the superoxide species by hindering one of the faces of the complex. However, the bond thus formed is weak. The grafting of the ligand via a covalent bond results, for its part, in a stronger material. Generally, the methods for the incorporation of the transition metal complexes in organic or inorganic matrices have to date been unable to result in materials which are compatible with the requirements of process engineering and can thus be used in industrial processes. In particular, the characteristics of such a material must be able to be adjusted in terms of specific surface, of porosity, whether this be the radius, the shape or the size distribution of the pores, and of particle size. The Applicant Company has found that the material which is a subject-matter of the present invention makes it possible to solve the problems set out hereinabove. A subject-matter of the invention is a compound of formula (I):

(I)

in which:

W$_1$, W$_2$ and W$_3$, which are identical or different, each represent, independently of one another, a divalent radical chosen from those represented by the general formula (A):

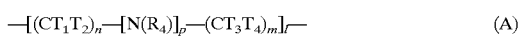

(A)

in which:

p represents an integer equal to 0 or to 1, l represents an integer equal to 1 or to 2, n and m, which are identical or different, each represent, independently of one another, an integer less than or equal to 3 and greater than or equal to 1, T$_1$, T$_2$, T$_3$ and T$_4$, which are identical or different, either each represent, independently of one another, a hydrogen atom, a linear or branched alkyl radical comprising from 1 to 15 carbon atoms or a [(hetero)aryl]alkyl radical comprising from 7 to 12 carbon atoms or else CT$_1$T$_2$ and/or CT$_3$T$_4$ represent a divalent group —(C=O)—, R$_4$ represents a hydrogen atom, a linear or branched alkyl radical comprising from 1 to 15 carbon atoms which is unsubstituted or substituted by one or more functional groups, a [(hetero)aryl]alkyl radical comprising from 7 to 12 carbon atoms or a radical represented by the general formula (B):

$$R_5—Si(X_1)(X_2)(X_3) \quad (B)$$

in which:

X$_1$, X$_2$ and X$_3$, which are identical or different, each represent, independently of one another, a hydrogen atom, a halogen atom or an OR$_6$ radical, in which R$_6$ represents a hydrogen atom or an alkyl radical comprising from 1 to 4 carbon atoms, R$_5$ represents a divalent radical derived from a saturated or unsaturated aliphatic hydrocarbonaceous chain comprising from 1 to 10 carbon atoms, in which chain are optionally inserted one or more structural links chosen from the arylene group or the —O—, —S—, —O—C(=O)—, —N(R$_7$)—C(=O)— or —N(R$_7$)— fragments, in which fragments R$_7$ represents a hydrogen atom, an aliphatic hydrocarbonaceous radical comprising from 1 to 6 carbon atoms, a benzyl radical or a phenethyl radical, said chain being unsubstituted or substituted by one or more radicals chosen from halogen atoms, the hydroxyl group, alkyl radicals comprising from 1 to 4 carbon atoms or benzyl or phenethyl radicals, R$_1$, R$_2$ and R$_3$, which are identical or different, each represent, independently of one another and of R$_4$, a hydrogen atom, a linear or branched alkyl radical comprising from 1 to 15 carbon atoms which is unsubstituted or substituted by one or more functional groups, a [(hetero)aryl]alkyl radical comprising from 7 to 12 carbon atoms or a radical represented by the general formula (B) as defined above, it being understood that at least one of these cyclic nitrogens is substituted by a radical of formula (B).

DETAILED DESCRIPTION OF THE INVENTION

Mention may be made, as compounds of formula (I) comprising three cyclic nitrogen atoms, of, for example, the compounds derived from 1,4,7-triazacyclononane, from 1,4,7-triazacyclodecane or from 1,5,8-triazacyclododecane. Mention may be made, as compounds of formula (I) comprising four cyclic nitrogen atoms, of, for example, the compounds derived from 1,4,7,10-tetraazacyclododecane (cyclene), from 1,4,7,10-tetraazacyclotridecane, from 1,4,7,10-tetraazacyclotetradecane, from 1,4,8,11-tetraazacyclotetradecane (cyclam), from 1,4,8,12-tetraazacyclopentadecane, from 1,5,9,13-tetraazacyclohexadecane or from 1,5,10,14-tetraazacyclooctadecane. Mention may be made, as compounds of formula (I) comprising five cyclic nitrogen atoms, of, for example, the compounds derived from 1,4,7,10,13-pentazacyclopentadecane, from 1,4,7,11,15-pentaazacyclooctadecane or from 1,5,9,13,17-pentaazacyclooctadecane.

Mention may be made, as compounds of formula (I) comprising six cyclic nitrogen atoms, of, for example, the compounds derived from 1,4,7,10,13,16-hexaazacyclooctadecane or from 1,5,9,13,17,20-hexaazacyclotetracosane.

The term "functional group" denotes in particular, in the definitions of R$_1$, R$_2$, R$_3$ and R$_4$, the carboxyl (CO$_2$H), carboxamido (CONH$_2$), sulfo (SO$_3$H) or dihydrophosphonato (PO$_3$H$_2$) groups, in the esterified form.

A particular subject-matter of the invention is, either a compound of formula (Ia), corresponding to the formula (I) as defined above in which W$_1$, W$_2$ and W$_3$, which are identical or different, represent a radical of formula (A$_1$), corresponding to the formula (A) as defined above in which p is equal to 0 and the sum n+m is equal to 2 or to 3, or a compound of formula (Ib), corresponding to the formula (I) in which W$_1$ represents a divalent radical of formula (A$_2$), corresponding to the formula (A) as defined above in which p is equal to 1 and the sum n+m is equal to 2 or to 3, and W$_2$ and W$_3$, which are identical or different, represent a radical of formula (A$_1$), or a compound of formula (Ic), corresponding to the formula (I) in which W$_1$ and W$_2$, which are identical or different, represent a divalent radical of formula (A$_2$) and W$_3$ represents a radical of formula (A$_1$).

A more particular subject-matter of the invention is, either the compound of formula (Ia$_1$), corresponding to the formula (Ia) as defined above in which l is equal to 1 and either W$_1$, W$_2$ and W$_3$ each represent the divalent radical —CH$_2$—CH$_2$—CH$_2$— or else any one of the three groups W$_1$, W$_2$ or W$_3$ represents the divalent radical —CH$_2$—CH$_2$—CH$_2$— and each of the other two groups represents the divalent radical —CH$_2$—CH$_2$—, or the compound of formula (Ib$_1$), corresponding to the formula (Ib) as defined above in which l is equal to 1 and either any one of the three groups W$_1$, W$_2$ or W$_3$ represents the radical —CH$_2$—CH$_2$—CH$_2$—N(R$_4$)—CH$_2$—CH$_2$—, either one of the two remaining groups represents the radical —CH$_2$—CH$_2$— and the final group represents the radical —CH$_2$—CH$_2$—CH$_2$— or else any one of the three groups W$_1$, W$_2$ or W$_3$ represents the radical —CH$_2$—CH$_2$—CH$_2$—N(R$_4$)—CH$_2$—CH$_2$—CH$_2$— and the other two groups each represent the radical —CH$_2$—CH$_2$—CH$_2$—.

The compound of formula (I) can be unsubstituted or substituted; when it is substituted, it is, for example, that substituted by one or more alkyl radicals comprising from 1 to 15 carbon atoms or the benzyl, picolyl or phenethyl radicals, such as, for example, 6-dodecyl-1,4,8,11-tetraazacyclotetradecane, 3-dodecyl-1,5,9,13-tetraazacyclohexadecane, 3-dodecyl-1,5,10,14-tetraazacyclooctadecane, 5,5,7,12,12,14-hexamethyl-1,4,8,11-tetraazacyclotetradecane, 1,4,7,10,13-pentaethyl-1,4,7,10,13,16-hexaazacyclooctadecane, 1,4,7,10-tetraethyl-1,4,7,10,13-pentaazacyclopentadecane, 1-methyl-1,4,8,11-tetraazacyclotetradecane, 1-benzyl-1,4,8,11-tetraazacyclotetradecane, 1-[(2-pyridyl)methyl]-1,4,8,11-tetraazacyclotetradecane, 1-[(3-pyridyl)methyl]-1,4,8,11-tetraazacyclotetradecane or 1,4-dibenzyl-1,4,8,11-tetraazacyclotetradecane.

According to a specific aspect of the present invention, a subject-matter of the latter is the compounds of formulae (Ia), (Ib) and (Ic) as defined above in which the R$_1$, R$_2$, R$_3$ and R$_4$ radicals represent either a (B) radical or a hydrogen atom and in particular the compounds of formulae (Ia$_1$) and (Ib$_1$) as defined above in which the R$_1$, R$_2$, R$_3$ and R$_4$ radicals represent either a (B) radical or a hydrogen atom.

According to another specific aspect of the present invention, a subject-matter of the latter is the compound of formula (I) as defined above in which R$_1$, R$_2$, R$_3$ and R$_4$ represent either a (B) radical or a radical —(CH$_2$)$_w$—C(=O)—V, in which V represents one of the NH$_2$ or OR$_8$ radicals, in which R$_8$ represents an alkyl radical comprising from 1 to 4 carbon atoms, and w represents an integer greater than or equal to 1 and less than or equal to 6.

The radical of formula (B) as defined above is, for example, a radical of formula (B$_1$):

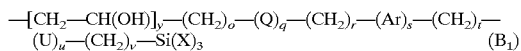
(B₁)

in which:
- o, r, t and v, which are identical or different, each represent, independently of one another, an integer greater than or equal to 0 and less than or equal to 6,
- y, q, s and u, which are identical or different, represent, independently of one another, an integer greater than or equal to 0 and less than or equal to 1,
- Q and U, which are identical or different, each represent, independently of one another, an oxygen atom, a sulfur atom or one of the —O—CO—, —CO—O—, —NH—CO—, —CO—NH— or —NH— groups,
- Ar represents an arylene group and in particular a phenylene group,
- X represents a hydrogen atom or one of the methoxy or ethoxy radicals, it being understood,
- that, when q is equal to 1, the sum y+o is other than 0,
- that, when q is equal to 1 and when u is equal to 0, the sum r+s+t+v is other than 0,
- that, when u is equal to 1, v is other than 0,
- that, when u is equal to 1 and when q is equal to 0, the sum y+o+r+s+t is other than 0,
- that, when s is equal to 0 and when q and u are each equal to 1, the sum r+t is other than 0, and
- that the sum y+o+r+t+v is less than or equal to 12.

In a preferred alternative form of the present invention, the radical of formula (B₁) as defined above is chosen from the 3-silylpropyl, (4-silylphenyl)methyl, 3-(triethoxysilyl)propyl, 3-[[3-(triethoxysilyl)propyl]oxy]-2-hydroxypropyl, [4-[[[3-(triethoxysilyl)propyl]amino]methyl]phenyl]methyl, [4-(triethoxysilyl)phenyl]propyl, 3-oxo-3-[[3-(triethoxysilyl)propyl]oxy]propyl or 2-oxo-2-[[3-(triethoxysilyl)propyl]amino]ethyl radicals.

A very particular subject-matter of the invention is the compounds with the following names:
- 1,4,8,11-tetrakis[3-(triethoxysilyl)propyl]-1,4,8,11-tetraazacyclotetradecane,
- 1,4,8,11-tetrakis[[4-(triethoxysilyl)phenyl]methyl]-1,4,8,11-tetraazacyclotetradecane,
- tetra[3-(triethoxysilyl)propyl]1,4,8,11-tetraazacyclotetradecane-1,4,8,11-tetrapropanoate,
- 1,4,8,11-tetrakis(3-silylpropyl)-1,4,8,11-tetraazacyclotetradecane,
- 1,4,8,11-tetrakis[(4-silylphenyl)methyl]-1,4,8,11-tetraazacyclotetradecane,
- N₁,N₂,N₃,N₄-tetrakis[3-(triethoxysilyl)propyl]-1,4,8,11-tetraazacyclotetradecane-1,4,8,11-tetraacetamide,
- 4,11-bis[[4-(triethoxysilyl)phenyl]methyl]-1,4,8,11-tetraazacyclotetradecane-7,14-dione.

According to another aspect of the present invention, a subject-matter of the latter is a process for the preparation of the compound of formula (I) as defined above, which comprises
a) the reaction of a compound of formula (C)

(C)

in which:
- X₁, X₂ and X₃, which are identical or different, each represent, independently of one another, a hydrogen atom, a halogen atom or an OR₆ radical, in which R₆ represents a hydrogen atom or an alkyl radical comprising from 1 to 4 carbon atoms,
- R'₅ represents a divalent radical derived from a saturated or unsaturated aliphatic hydrocarbonaceous chain comprising from 1 to 10 carbon atoms, in which chain are optionally inserted one or more structural links chosen from the arylene group or the —O—, —S—, —O—C(=O)—, —N(R₇)—C(=O)— or —N(R₇)— fragments, in which fragments R₇ represents a hydrogen atom, an aliphatic hydrocarbonaceous radical comprising from 1 to 6 carbon atoms, a benzyl radical or a phenethyl radical, said chain being unsubstituted or substituted by one or more radicals chosen from halogen atoms, the hydroxyl group, alkyl radicals comprising from 1 to 4 carbon atoms or the benzyl or phenethyl radicals,
- Z represents a functional group capable of reacting with a secondary amine functional group, =N—H, to form an N—C covalent bond, with a compound of formula (I'):

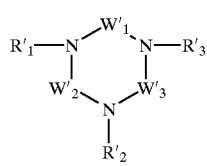

in which:
- W'₁, W'₂ and W'₃, which are identical or different, each represent, independently of one another, a divalent radical chosen from those represented by the general formula (A'):

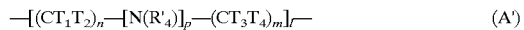
(A')

in which,
- l, p, n, m, T₁, T₂, T₃ and T₄ have the same definition as for the formula (A) as defined above and
- R'₄ represents a hydrogen atom, a linear or branched alkyl radical comprising from 1 to 15 carbon atoms or a [(hetero)aryl]alkyl radical comprising from 7 to 12 carbon atoms,
- R'₁, R'₂ and R'₃, which are identical or different, each represent, independently of one another and of R₄, a hydrogen atom, a linear or branched alkyl radical comprising from 1 to 15 carbon atoms or a [(hetero)aryl]alkyl radical comprising from 7 to 12 carbon atoms, it being understood that the polyazacycloalkane nucleus of the compound of formula (I) comprises at most 30 cyclic carbon atoms and at most 6 cyclic nitrogen atoms and that at least one of these cyclic nitrogen atoms is to form the compound of formula (I) as defined above and, if desired, b) the functionalization of all or a portion of the unsubstituted cyclic nitrogens of said compound of formula (I) to form a compound of formula (Id), corresponding to the formula (I) as defined above in which at least one of the R₁, R₂, R₃ or R₄ radicals represents a radical —(CH₂)_w—C(=O)—V in which w and V are as defined above.

The term "functional group capable of reacting with a secondary amine" denotes in particular those which react according to a nucleophilic substitution mechanism, such as, for example, halogen radicals and in particular the bromo or iodo radicals, or those which react according to an electrophilic addition mechanism, such as, for example, the epoxy functional group, which results in an N—CH₂—CH(OH)— fragment; it can also be a free, salified or esterified carboxyl functional group or an unsaturated group CH₂=CH—, which results in an N—CH₂—CH₂— fragment by a reaction of "Michael" type according to a nucleophilic addition mechanism.

These examples do not have a limiting nature and it is obvious that any functional group known to a person skilled in the art at the date of filing of the present patent application as being capable of reacting with a secondary amine functional group to form an N—C covalent bond forms an integral part of the description of the present invention.

The compounds of formula ($C_1$):

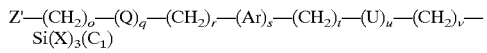

in which:
o, q, r, s, t, u, v, Q, Ar, U and X have the same definition as for the formula ($B_1$) as defined above, Z' represents either a halo radical, in particular a bromo radical or an iodo radical, or an oxiran-2-yl group or an ethenyl group, the sum q+s is equal to 0 or to 1, it being understood that, when q is equal to 1 and when Z' represents a halo radical, o is other than 0, that, when q is equal to 1 and when u is equal to 0, the sum r+s+t+v is other than 0, that, when u is equal to 1, v is other than 0, that, when u is equal to 1 and when q is equal to 0, the sum o+r+s+t is other than 0, that, when s is equal to 0 and when q and u are each equal to 1, the sum r+t is other than 0, and that the sum o+r+t+v is less than 6, and in particular (triethoxy)(3-iodopropyl)silane, 2-[[[3-(triethoxysilyl)propyl]oxy]methyl]oxirane, N-[[4-(bromomethyl)phenyl]methyl]—N-[3-(triethoxysilyl)propyl]amine, (triethoxy)[4-(iodomethyl)phenyl]silane, 3-(triethoxysilyl)propyl propenoate or N-[3-(triethoxysilyl)propyl]bromoacetamide, are particularly appropriate in carrying out the process according to the invention.

According to another aspect of the present invention, a subject-matter of the latter is a polysiloxane gel (III) incorporating polyazamacrocycles and metal complexes of these nitrogenous ligands, which is capable of being obtained from the hydrolysis of the compound of formula (I) as defined above, resulting in the formation of a polysiloxane gel incorporating non-metallated polyazamacrocycle units (III'), followed by the action of a metal salt on said gel (III'), and the process for the preparation of the polysiloxane gel (III') thus carried out starting from the compound of formula (I) as defined above.

According to another aspect of the present invention, a subject-matter of the latter is a polysiloxane gel (IV) incorporating polyazamacrocycles and metal complexes of these nitrogenous ligands, which is capable of being obtained from the action of a metal salt on the compound of formula (I) as defined above, resulting in the formation of an organometallic complex of said metal with said compound of formula (I), followed by the hydrolysis of said organometallic complex, and the process for the preparation of polysiloxane gel (IV) thus carried out starting from the compound of formula (I) as defined above.

The metal involved in the composition of the polysiloxane gel (III) or (IV) is chosen in particular from U, Pu, Am, Eu, Ce, Cr, Gd, Mn, Fe, Co, Ni, Cu, Zn, Ag, Cd, Au, Hg or Pb.

A more particular subject-matter of the present invention is hybrid materials ($III_4$) and ($IV_1$), corresponding respectively to the hybrid compounds (III) and (IV) in which the metal element is chosen from cobalt or copper, and more particularly materials ($III_{1a}$) and ($IV_{1a}$) capable of being obtained from the compound of formula (Ia), (Ib) or (Ic).

In a final aspect of the present invention, a subject-matter of the latter is the use of these metallated hybrid gels as defined above in separating a predetermined gas from a mixture of gases, wherein said mixture of gases is brought into contact with one of the metallated hybrid gels (III) or (IV) as defined above under conditions which make possible the absorption of said gas to be separated, followed by a phase of desorption of said gas attached to said gel and by a phase of recovery of said desorbed gas. This use is preferably applied to the separation of oxygen from the air, either for the purpose of producing pure oxygen or for the purpose of removing oxygen from the air.

The non-metallated gels (III') can be employed in purifying liquids which absolutely have to be free from any metal cation, in particular those used in the electronics industry, such as, for example, dilute or concentrated hydrogen peroxide.

The non-metallated gels (III') can also be employed in purifying gases by adsorption of the undesirable gaseous impurities The following examples illustrate the invention and in particular the two routes described above for the synthesis, according to a sol-gel process, of novel polysiloxanes incorporating polyazacycloalkanes and metal complexes of these nitrogenous ligands.

As shown in these examples, the variety of the precursors used, the optional addition of tetraalkoxysilane during the gelling stage and the variations in the operating conditions make it possible to obtain materials with a variable composition and a variable texture, both in terms of concentration of ligand or of complex in the solid and of porosity and specific surface. Under strictly identical synthesis conditions, the solids obtained exhibit identical characteristics, thus showing good reproducibility of the method.

The advantages of this method thus lie essentially in the possibility of adjusting the characteristics of the material according to the requirements of materials engineering.

EXAMPLES

Various silica gels were synthesized by choosing 1,4,8,11-tetraazacyclotetradecane (or cyclam) as organic ligand for the coordination of the metal element. The various precursors were obtained, according to the following scheme, by reaction of the cyclam with four equivalents of various silylated reactants of formula (C) to form the corresponding compounds of formula (I). Several substituents terminating in an —Si(OEt)$_3$ or —SiH$_3$ group were used: an aliphatic chain or substituents comprising an aromatic unit or an ester or amide functional group.

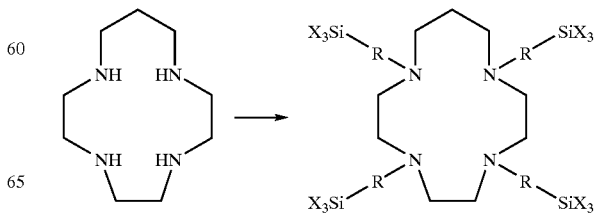

-continued

R = [structures shown: butyl chain; p-methylbenzyl; butyl propanoate (ester); butyl propanamide (amide)]

X = OEt, H

The following compounds were thus prepared:

Compound 1
1,4,8,11-Tetrakis[3-(triethoxysilyl)propyl]-1,4,8,11-tetraazacyclotetradecane 2 g (0.01 mol) of cyclam and 12.41 g (0.09 mol) of $K_2CO_3$ in 100 ml of $CH_3CN$ (distilled over $P_2O_5$) are placed in a 200 ml Schlenk tube under a nitrogen atmosphere. 13.27 g (0.04 mol) of (triethoxy) (3-iodo-propyl)silane are then added. The reaction mixture is brought to reflux for 12 h. After evaporating the solvent, the residue is taken up in 100 ml of pentane and filtered, and the precipitate is washed twice with 30 ml of pentane. The filtrates are combined, the pentane is evaporated and compound 1 is obtained in the form of a slightly cloudy oil (9.85 g, 97%).

$^1$H NMR (200 MHz, $CDCl_3$) δ (ppm): 0.58 (m, 8H), 1.23 (t, 36H), 1.55 (m, 12H), 2.39 (m, 8H), 2.51 (m, 8H), 2.54 (s, 8H), 3.83 (q, 24H). $^{13}$C NMR (50 MHz, $CDCl_3$) δ (ppm): 7.0, 17.3, 19.6, 21.9, 49.5, 50.4, 57.3, 57.9. $^{29}$Si NMR (40 MHz, $CDCl_3$) δ (ppm): −44.6. Elemental analysis for $C_{46}H_{104}N_4O_{12}Si_4$; Calculated: C. 54.33; H. 10.24; N. 5.51. Found: C. 53.9; H. 9.93; N. 6.27.

Compound 2
1,4,8,11-Tetrakis[[4-(triethoxysilyl)phenyl]methyl]-1,4,8,11-tetraazacyclotetradecane By carrying out the preparation in the same way as for compound 1, from 1.5 g (0.0075 mol) of cyclam, 9.32 g (0.0675 mol) of $K_2CO_3$ and 11.4 g (0.03 mol) of (triethoxy)[4-(iodomethyl)phenyl]silane, a beige solid is obtained and, after recrystallization from 15 ml of ethanol, compound 2 is obtained in the form of a white powder (6.5 g, 72%). M.p.=99.5–100.5° C. $^1$H NMR (200 MHz, $CDCl_3$) δ (ppm): 1.29 (t, 36H), 1.77 (m, 4H), 2.54 (t, 8H), 2.63 (s, 8H), 3.46 (s, 8H), 3.90 (q, 24H), 7.34 (d, 8H), 7.60 (d, 8H). $^{13}$C NMR (50 MHz, $CDCl_3$) δ (ppm): 18.6, 24.4, 50.8, 51.9, 59.1, 59.8, 128.8, 129.3, 135.0, 142.9. $^{29}$Si NMR (40 MHz, $CDCl_3$) δ (ppm): −56.9. Elemental analysis for $C_{62}H_{104}N_4O_{12}Si_4$; Calculated: C. 61.58; H. 8.61; N. 4.63; Found: C. 61.45; H. 8.81; N. 4.59.

Compound 3
Tetra[3-(triethoxysilyl)propyl]1,4,8,11-tetraazacyclotetradecane-1,4,8,11-tetrapropanoate 0.5 g (0.0025 mol) of cyclam in 20 ml of ethanol are placed in a 100 ml Schlenk tube under a nitrogen atmosphere. 2.76 g (0.01 mol) of 3-(triethoxysilyl)propyl acrylate are then added. The reaction mixture is brought to reflux for 12 h. After evaporating the solvent, a cloudy oil is obtained, which oil is taken up in 10 ml of pentane and left for 1 h at −20° C. The white precipitate formed is filtered, the filtrate is concentrated and compound 3 is obtained in the form of a clear oil (2.36 g, 72%).

$^1$H NMR (200 MHz, $CDCl_3$) δ (ppm): 0.51 (m, 8H), 1.24 (t, 36H), 1.44 (m, 4H), 1.61 (m, 8H), 2.35 (t, 8H), 2.41 (t, 8H), 2.44 (s, 8H), 2.61 (t, 8H), 3.69 (q, 24H), 3.90 (t, 8H). $^{13}$C NMR (50 MHz, $CDCl_3$) δ (ppm): 6.9, 18.7, 22.6, 24.5, 32.9, 50.8, 51.1, 51.5, 58.7, 66.7, 173.1. $^{29}$Si NMR (40 MHz, $CDCl_3$) δ (ppm): −45.6. Elemental analysis for $C_{58}H_{120}N_4O_2OSi_4$; Calculated: C. 53.37; H. 9.20; N. 4.29; Found: C. 53.17; H. 9.18; N. 4.85.

By carrying out the preparation in the same way as hereinabove with 2-(triethoxysilyl)ethyl acrylate, tetra[2-(triethoxysilyl)ethyl]1,4,8,11-tetraazacyclotetradecane-1,4,8,11-tetrapropanoate (compound 8) is obtained.

Compound 4
1,4,8,11-Tetrakis(3-silylpropyl)-1,4,8,11-tetraazacyclotetradecane 7.47 g (0.00735 mol) of the compound obtained in Example 1 in 40 ml of anhydrous ether are placed in a 150 ml Schlenk tube under a nitrogen atmosphere. A solution of 1.68 g (0.041 mol) of $LiAlH_4$ in 30 ml of anhydrous ether is then added dropwise at 0° C. The reaction mixture is stirred for 24 h at room temperature and then excess $LiAlH_4$ is destroyed with 5.5 ml of ethyl acetate at 0° C. After 30 min at room temperature, the solvents are evaporated. The residue is taken up in pentane, the solid is filtered off and washed twice with pentane, and compound 4 is obtained in the form of an oil (2.83 g, 80%).

$^1$H NMR (200 MHz, $CDCl_3$) δ (ppm): 0.74 (m, 8H), 1.57 (m, 12H), 2.42 (t, 8H), 2.52 (t, 8H), 2.55 (s, 8H), 3.53 (t, 12H). $^{13}$C NMR (50 MHz, $CDCl_3$) δ (ppm): 2.8, 21.9, 23.1, 49.5, 50.5, 56.9. $^{29}$Si NMR (40 MHz, $CDCl_3$) δ (ppm): −58.7.

Compound 5
1,4,8,11-Tetrakis[(4-silylphenyl)methyl]-1,4,8,11-tetraazacyclotetradecane 3.75 g (0.0031 mol) of the compound obtained in Example 2 in 50 ml of THF are placed in a 200 ml Schlenk tube under a nitrogen atmosphere. A solution of 0.70 g (0.018 mol) of $LiAlH_4$ in 20 ml of THF is then added dropwise at 0° C. The reaction mixture is stirred for 1 h at 0° C. and then for 12 h at room temperature. The excess $LiAlH_4$ is destroyed with 3 ml of ethyl acetate. The reaction mixture is filtered through 20 g of Florisil® and the solvent is evaporated. The residue is taken up in 50 ml of $CH_2Cl_2$ and filtered, and then the solvent is evaporated. 1.41 g of compound 5 are obtained in the form of a white powder (70%).

$^1$H NMR (200 MHz, $CDCl_3$) δ (ppm): 1.77 (m, 4H), 2.55 (t, 8H), 2.63 (s, 8H), 3.45 (d, 8H), 4.23 (s, 12H), 7.32 (d, 8H), 7.51 (d, 8H). $^{13}$C NMR (50 MHz, $CDCl_3$) δ (ppm): 25.3, 51.0, 51.9, 59.8, 126.5, 129.1, 136.1, 142.4. $^{29}$Si NMR (40 MHz, $CDCl_3$) δ (ppm): −59.3. Elemental analysis for $C_{38}H_{56}N_4Si_4$; Calculated: C. 67.06; H. 8.24; N. 8.24; Found: C. 66.76; H. 8.00; N. 8.06.

Compound 6
$N_1,N_2,N_3,N_4$-Tetrakis[3-(triethoxysilyl)propyl]-1,4,8,11-tetraazacyclotetradecane-1,4,8,11-tetraacetamide a) 38.2 ml (0.16 mol) of aminopropyltriethoxysilane and 23.6 ml (0.17 mol) of triethylamine are dissolved in 70 ml of $CH_2Cl_2$ in a 150 ml Schlenk tube and then a spatula tip of 4-dimethylaminopyridine (DMAP) is added. 26.95 g (0.17 mol) of bromoethanoyl chloride dissolved in 20 ml of $CH_2Cl_2$, are added dropwise at −30° C with stirring. The red viscous solution obtained is stirred for 2 h at room temperature and then the solvent is evaporated. The residue is taken up in 150 ml of ether; the salts are filtered off and the solvent is evaporated. 48.84 g of a very viscous brown product are obtained, which product, by distillation (127–132°/0.05 mm), results in 11.71 g (20%) of 2-bromo-N-[3-(triethoxysilyl)propyl]acetamide [$BrCH_2CONH(CH_2)_3Si(OEt)_3$].

b) 0.5 g (0.0025 mol) of cyclam, 25 ml of acetonitrile and 3.1 g of K$_2$CO$_3$ (0.0022 mol) are introduced into a 60 ml Schlenk tube. 3.76 g (0.011 mol) of the 2-bromo-N-[3-(triethoxysilyl)propyl]-acetamide prepared in stage a) are added dropwise with stirring. The reaction mixture is brought to reflux for 20 h. The solvent is subsequently evaporated. The residue is washed with 2×30 ml of warm pentane and is then taken up in 70 ml of CH$_2$Cl$_2$. After filtrating and evaporating CH$_2$Cl$_2$, 1.59 g (51%) of compound 6 are recovered in the form of a white powder.

$^1$H NMR (200 MHz, CDCl$_3$) δ (ppm): 0.64 (t, 8H), 1.23 (t, 36H), 1.63 (m, 12H), 2.64 (m, 16H), 3.04 (s, 8H), 3.26 (m, 8H), 3.81 (q, 24H), 7.06 (m, 4H). $^{13}$C NMR (50 MHz, CDCl$_3$) δ (ppm): 8.4, 18.7, 23.9, 24.9, 42.1, 51.4, 52.6, 58.8, 59.1, 170.9. $^{29}$Si NMR (40 MHz, CDCl$_3$) δ(ppm): −45.8. Elemental analysis for C$_{54}$H$_{116}$N$_8$O$_{16}$Si$_4$; Calculated: C. 52.09; H. 9.32; N. 9.00; Found: C. 49.55; H. 8.78; N. 9.34.

Compound 7
4,11-Bis[[4-(triethoxysilyl)phenyl]methyl]-1,4,8,11-tetraazacyclotetradecane-7,14-dione 2 g (0.0088 mol) of 7,14-dioxocyclam, 3.63 g (0.0026 mol) of K$_2$CO$_3$ and 70 ml of anhydrous acetonitrile are introduced into a 200 ml Schlenk tube. 6.7 g (0.018 mol) of (triethoxy)[(4-iodophenyl)methyl]silane are added dropwise. The reaction mixture is brought to reflux for 12 h. The solvent is subsequently evaporated, the precipitate obtained is taken up twice in 70 ml of CH$_2$Cl$_2$ and the solution is filtered. The solvent is evaporated and the solid is washed twice with 50 ml of pentane. 5.46 g of compound 7 are obtained in the form of a white powder which recrystallizes from a CH$_2$Cl$_2$/hexane (50/50) mixture. Yd 85%. M.p. 163–164° C.

$^1$H NMR (200 MHz, CDCl$_3$) δ (ppm): 1.23 (t, 18H), 2.44 (m, 4H), 2.69 (m, 8H), 3.44 (m, 4H), 3.71 (s, 4H), 390 (q, 12H), 7.28 (d, 4H), 7.68 (d, 4H). $^{13}$C NMR (50 MHz, CDCl$_3$) δ (ppm): 18.6, 32.6, 36.2, 49.6, 52.5, 57.8, 59.2, 129.5, 131.2, 135.4, 138.7, 172.5. $^{29}$Si NMR (40 MHz, CDCl$_3$) δ (ppm): −57.9. Elemental analysis for C$_{36}$H$_{60}$N$_4$O$_8$Si$_2$; Calculated: C. 59.01; H. 8.20; N. 7.65. Found: C. 58.91; H. 8.11; N. 7.73.

The hydrolysis of these compounds of formula (I) according to Route A or of the corresponding metal complexes (Route B) results in solids (III) and (IV) which exhibit different textures:

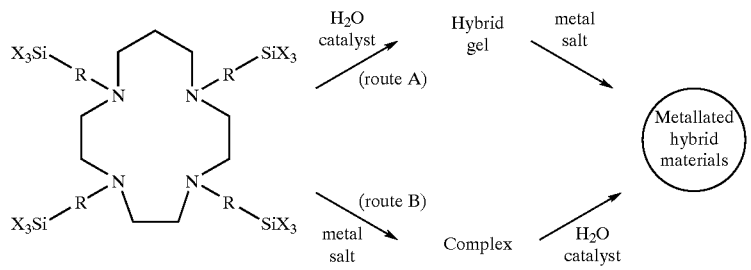

Cyclams carrying a single substituent with an —Si(OEt)$_3$ ending which substituted or unsubstituted on the three remaining secondary amine functional groups have also been involved in a gelling process according to the following reaction:

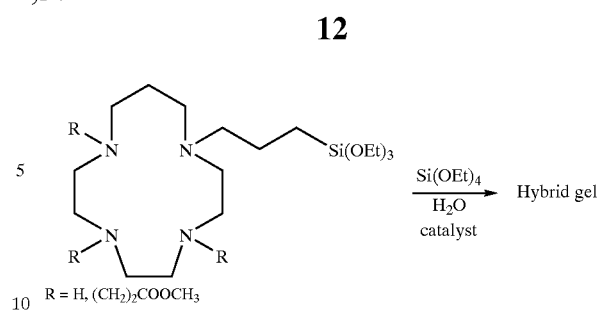

R = H, (CH$_2$)$_2$COOCH$_3$

In this case, the addition of tetraethoxysilane is necessary for the polymerization of the precursor. A cogel is then obtained. This cogelling was also carried out in the other cases in order to study the influence of the addition of Si(OEt)$_4$ in variable proportions on the texture of the material obtained. The other gelling factors studied are the nature of the solvent (MeOH, EtOH, THF, CH$_2$Cl$_2$, HCONH$_2$), the concentration of the precursor (0.05 to 4 mol/dm$^3$), the presence or the absence of catalyst (NH$_3$ or tetraalkylammonium fluoride, such as TBAF) and the temperature (−20° C. to 150° C). The results are recorded in the following Table 1; they show that, according to the gelling conditions, more or less condensed gels are obtained, this property being deduced from a $^{29}$Si NMR study in the solid state; the degree of condensation increases in the order T$^0$<T$^1$<T$^2$<T$^3$ (Shea K. J., Loy D. A., Webster O. W.; *Chem Mater.*, 1989, 1, 572–574). They also show, by BET analysis, that these more or less condensed gels exhibit different specific surfaces and different porosities.

In the case of a precursor of formula (I) comprising several cyclic nitrogen atoms substituted by radical of general formula (B) as defined above, cogels are also prepared by addition of tetraalkoxysilanes, such as, for example, tetraethoxysilane.

| Influence of the solvent (1M/TBAF/20° C.) | | | | |
|---|---|---|---|---|
| (a) | EtOH | 17 min | 370 m$^2$/g | T$^3$ > T$^2$ |
| (b) | THF | 27 min | 343 m$^2$/g | |
| (c) | HCONH$_2$ | 30 min | 2 m$^2$/g | |

-continued

| | | | | |
|---|---|---|---|---|
| (d) | CH$_2$Cl$_2$ | 55 min | 454 m$^2$/g | |
| Influence of the concentration (EtOH/TBAF/20° C.) | | | | |
| (a) | 1M | 17 min | 370 m$^2$/g | T$^3$ > T$^2$ |
| (e) | 2M | 10 min | 470 m$^2$/g | T$^3$ ~ T$^2$ |
| (f) | 3M | 7 min | 414 m$^2$/g | T$^3$ > T$^2$ |

-continued

| | | Influence of the catalyst (EtOH/1M/20° C.) | | |
|---|---|---|---|---|
| (g) | without | 36 h | 2 m²/g | $T^0 > T^1 \sim T^2 \sim T^3$ |
| (a) | TBAF | 17 min | 370 m²/g | $T^3 > T^2$ |
| (h) | TBAF (sono) | 15 min | 410 m²/g | $T^3 > T^0 \sim T^1 \sim T^2$ |
| (i) | $NH_3$ | <24 h | 0 m²/g | |
| | | Influence of the temperature (EtOH/TBAF/1M) | | |
| (a) | 20° C. | 17 min | 370 m²/g | $T^3 > T^2$ |
| (j) | 100° C. | <30 min | ~800 m²/g | |
| | | Dilution with n Si(OEt)₄ (EtOH/TBAF/1M/20° C.) | | |
| (a) | n = 0 | 17 min | 370 m²/g | $T^3 > T^2$ |
| (k) | n = 1 | <30 min | 386 m²/g (292ª + 95ᵇ) | $T^3 > T^2 \; Q^3 = Q^4$ |
| (l) | n = 2 | <30 min | 428 m²/g (290ª + 138ᵇ) | $T^3 < T^2 \; Q^3 = Q^4$ |
| (m) | n = 5 | <30 min | 515 m²/g (299ª + 216ᵇ) | |
| Si(OEt)₄ | | 3–4 h | 470 m²/g (296ª + 174ᵇ) | |

ªMicroporous surface
ᵇExternal surface

TABLE 1

Factors influencing the texture of gels obtained by hydrolysis (6H₂O) of

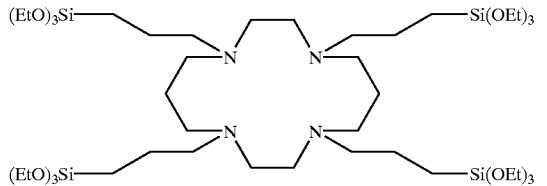

Materials with different textures were obtained from the precursor compounds (1) to (7). According to the experimental conditions (starting precursor, temperature, solvent, catalyst), it was possible to obtain materials with predetermined specific surfaces ranging from 10 m²/g to 800 m²/g, it being possible for the solids to be microporous, mesoporous or both simultaneously. The results are recorded in Table 2:

TABLE 2

Influence of the nature of the substituents on the texture of the material

| Precursor compound | 20° C./EtOH | 20° C./THF | 20° C./CH₂Cl₂ | 100° C./EtOH | 100° C./CH₂Cl₂ |
|---|---|---|---|---|---|
| (1) | 370 m²/g micropores gel (a) | 350 m²/g micropores gel (b) | 460 m²/g micropores gel (d) | 800 m²/g mesopores gel (j) | |
| (2) | <10 m²/g | — | 200 m²/g micropores mesopores gel (r₁) | — | 400 m²/g gel (r₂) |
| (3) | <10 m²/g gel (s) | — | — | — | — |
| (6) | <10 m²/g gel (t) | — | — | — | — |
| (4) | — | 350 m²/g micropores mesopores gel (u) | — | — | — |
| (5) | — | <10 m²/g gel (v) | — | — | — |

Several metal salts were used for the metallation, before or after gelling. They are Cu(OAc)₂, CuCl₂, Cu(BF₄)₂, Cu[B(C₆H₅)₄]₂, Cu[(PF₆)]₂, CuSiF₆, Co(OAc)₂, CoCl₂, Co(BF₄)₂, Co[B(C₆H₅)₄]₂, Co[PF₆]₂ and CoSiF₆. The amount of metal in the metallated gels was determined by X-ray fluorescence spectroscopy. The results are recorded in Tables 3 to 6.

TABLE 3

Metallation of the gels and cogels with CuCl₂ (Route A)

| Gel | Specific surface before metallation (m²/g) | Ligand/metal stoichiometry | Specific surface after metallation (m²/g) | [Cu⁺⁺] (mmol/g) |
|---|---|---|---|---|
| gel (j) | 800 (mesopores) | 1/2 | 80 | 1.33 |
| gel (j) | 800 | 1/1 | 250 | 0.83 |
| gel (a) | 370 (micropores) | 1/2 | <10 | 1.31 |
| gel (a) | 370 | 1/1 | <10 | 1.02 |
| gel (g) | <10 | 1/2 | <10 | 1.33 |
| gel (g) | <10 | 1/1 | <10 | — |
| gel (k) | 390 | 1/2 | <10 | 1.46 |
| gel (l) | 430 | 1/2 | <10 | 1.25 |
| gel (m) | 510 | 1/2 | 15 | 0.74 |
| gel (n) | 690 | 1/2 | 550 | 0.59 |
| gel (n) | 690 | 1/1 | 625 | — |
| gel (o) | 690 | 1/2 | 410 | — |
| gel (o) | 690 | 1/1 | 550 | — |
| gel (p) | 470 | 1/2 | 450 | 0 |
| gel (r₂) | 400 | 1/1 | <10 | 0.92 |
| gel (r₁) | 200 | 1/2 | <10 | 1.59 |
| gel (u) | 350 | 1/2 | 100 | 1.78 |
| gel (v) | <10 | 1/2 | <10 | 0.55 |

TABLE 4

Metallation of the gels with various Cu(II) salts (influence of the counterion) (Route A)

| Gel | Specific surface before metallation (m²/g) | Metal salt | Specific surface after metallation (m²/g) | [Cu⁺⁺] (mmol/g) |
|---|---|---|---|---|
| gel (j) | 800 (mesopores) | $CuCl_2$ | 250 | 0.83 |
| gel (j) | 800 (mesopores) | $CuSiF_6$ | <10 | — |
| gel (j) | 800 (mesopores) | $Cu(OAc)_2 \cdot H_2O$ | 280 | 0.85 |
| gel (a) | 370 (micropores) | $CuCl_2$ | <10 | 1.02 |
| gel (a) | 370 (micropores) | $CuSiF_6$ | <10 | — |
| gel (a) | 370 (micropores) | $Cu(OAc)_2 \cdot H_2O$ | <10 | — |
| gel (a) | 370 (micropores) | $2Cu(OAc)_2 \cdot 2H_2O$ | <10 | 1.27 |
| gel (g) | <10 | $CuCl_2$ | <10 | — |
| gel (g) | <10 | $CuSiF_6$ | <10 | — |
| gel (g) | <10 | $Cu(OAc)_2 \cdot H_2O$ | <10 | — |
| gel (g) | <10 | $2Cu(OAc)_2 \cdot 2H_2O$ | <10 | 1.44 |

TABLE 5

Metallation of the gels and cogels with $CoCl_2$ (Route A)

| Gel | Specific surface before metallation (m²/g) | Ligand/metal stoichiometry | Specific surface after metallation (m²/g) | [Co⁺⁺] (mmol/g) |
|---|---|---|---|---|
| gel (j) | 800 (mesopores) | 1/2 | 500 | 1.38 |
| gel (j) | 800 (mesopores) | 1/1 | 600 | 0.95 |
| gel (a) | 370 (micropores) | 1/2 | <10 | — |
| gel (a) | 370 (micropores) | 1/1 | 200 | 0.95 |
| gel (m) | 510 | 1/2 | 320 | 0.86 |
| gel (r₁) | 200 | 1/2 | 100 | 1.5 |
| gel (r₁) | 200 | 1/1 | — | 0.66 |
| gel (u) | 350 | 1/2 | 250 | 1.62 |
| gel (v) | <10 | 1/2 | <10 | 1.56 |

TABLE 6

Gelling at 20° C. of complexed precursors (Route B)

| Precursor compound | Metal of the precursor compound/metal complex | Specific surface (m²/g) | [Metal] (mmol/g) |
|---|---|---|---|
| compound 1 | Cu | <10 | 0.95 |
| compound 1 | Co | 10–20 | 0.90 |
| compound 2 | Cu | <10 | 0.97 |

The general experimental conditions are as follows:
Metallation of the Precursors)

The precursors are metallated with one or two equivalent(s) of metal salt at reflux for 24 h. The solids obtained are washed with pentane and then dried under vacuum.

Synthesis of the Gels

The precursor, the solvent, the necessary amount of water and the catalyst are placed in that order in a pill machine.

The gelling time $t_g$ is measured from the moment when all the reactants have been introduced.

Three different treatments were subsequently applied to the gels obtained:

a) aging for 5 days at room temperature, milling for 1 min, washing with ethanol and with diethyl ether, and then drying at 120° C./3–20 mmHg for 12 h b) aging for 2 days at room temperature and then the same treatment as a)

c) aging for 5 days at 100° C. (gellings in sealed tubes) and then the same treatment as a)

Metallation of the Gels

The metallations are carried out according to two methodologies:

a) Cu(II) complexes

The material and the copper salt (1 or 2 eq.) are placed in 20 ml of absolute ethanol in a 100 ml round-bottomed flask. The reaction mixture is brought to reflux for 12 h and the metallated material is filtered off, washed with ethanol and diethyl ether and, finally, dried at 120° C./3–20 mmHg for 12 h.

b) Co(II) complexes

The material and the cobalt salt (1 or 2 eq.) are placed in 20 ml of distilled ethanol in a 100 ml Schlenk tube under a nitrogen atmosphere. The reaction mixture is brought to reflux for 12 h and the metallated material is filtered off and washed with ethanol.

Gelling of the Metallated Precursors

The metallated precursors are gelled according to a procedure identical to the gelling of the non-metallated precursors.

During the gelling stages described hereinabove, use is generally made of the following solvents:

dimethylformamide (DMF), ethanol, methanol, tetrahydrofuran (THF), acetonitrile, dioxane or acetic acid;

the catalyst is generally chosen from acidic catalysts (H⁺), basic catalysts (OH⁻) or nucleophilic catalysts, such as F⁻ in the form of ammonium fluoride or of tetrabutylammonium fluoride, N,N-dimethyl-aminopyridine (DMAP), N-methylimidazole or hexamethylphosphoramide (HMPA).

Several oxygenation tests on metallated gels were carried out using an automatic adsorption bench tester based on the volumetric principle. The results are recorded in Table 7.

TABLE 7

| Gel | Metal salt Ligand/metal stoichiometry | Specific surface (m²/g) | [Co⁺⁺] (mmol/g) | Volume $O_2$ adsorbed (Scc/g) |
|---|---|---|---|---|
| gel (o) | $CoCl_2$ 1/1 | 690 | 0.19 | 1.23 |
| gel (a) | $CoCl_2$ 1/1 | 600 | 0.95 | 1.70 |
| gel (j) | $CoCl_2$ 1/1 | 200 | 0.95 | 2.30 |

A novel series of gels and/or cogels was prepared and the reactivity of these materials with respect to dioxygen and dinitrogen was studied by measuring the adsorption at 294K of said gases, by the decrease in the pressure at constant volume, using a Micromeritics adsorption bench tester.

The results are recorded in the following table:

TABLE 8

| Precursor | Gel (BET in m²·g⁻¹) | Metal | Counterion | Degassing 10⁶ torr | $N_2$ Scc/g | $O_2$ Scc/g | $[M^{2+}]$ mmol/g | $O_2/N_2$ Selectivity |
|---|---|---|---|---|---|---|---|---|
| Compound (1) | (1a) (480, (meso)) | $Cu^{2+}$ | 2 Cl⁻ | 1st cycle: 20° C., 24 h | 0.40 | 6.19 | 0.86 | 15.5 |
| | | | | 2nd cycle: 20° C., 3 h | | 1.57 | | 3.9 |
| Compound (1) | (1b) (75, (meso)) | $Cu^{2+}$ | 2 Cl⁻ | 1st cycle: 20° C., 24 h | 0.18 | 4.61 | 1.00 | 25.6 |
| | | | | 2nd cycle: 20° C., 18 h | | 2.50 | | 13.8 |
| Compound (1) | (1c) | $Cu^{2+}$ | 2 Cl⁻ | 1st cycle: 20° C., 24 h | 0.40 | 7.01 | 1.12 | 17.5 |
| | | | | 2nd cycle: 120° C., 24 h | nd | 11.07 | | 27.6 |
| | | | | 3rd cycle: 120° C., 24 h | 0.35 | 7.20 | | 20.6 |
| Compound (1) + 10 Si(OEt)₄ | (1d) | ½Cu²⁺ | Cl⁻ | 1st cycle: 20° C., 24 h | 0.45 | 0.47 | 0.21 | 1 |
| | | | | 2nd cycle: 120° C., 24 h | 0.54 | 0.75 | | 1.38 |
| Compound (1) | (1e) | $Co^{2+}$ | 2 Cl⁻ | 1st cycle: 20° C., 24 h | 0.51 | 0.51 | 1.49 | 1 |
| | | | | 2nd cycle: 120° C., 24 h | 0.41 | 0.43 | | 1 |
| Compound (1) | (1f) (417, (meso)) | ½ Co²⁺ | Cl⁻ | 20° C., 24 h | 0.61 | 0.66 | 1.05 | 1.08 |
| Compound (8) + 10 Si(OEt)₄ | (8a) (cogel) (250, (meso)) | ½ Co²⁺ | Cl⁻ | 1st cycle: 120° C., 24 h | nd | 1.54 | 0.35 | nd |
| | | | | 2nd cycle: 100° C., 2 h | nd | 1.49 | | nd |
| Compound (2) | (2a) | $Co^{2+}$ | 2 Cl⁻ | 20° C., 24 h | nd | 0.66 | 1.64 | nd |
| Compound (9) | (9a) | $Co^{2+}$ | 2 Cl⁻ | 1st cycle: 20° C., 24 h | 1.0 | 1.46 | 1.57 | 14.6 |
| | | | | 2nd cycle: 120° C., 3 h | 1.0 | 0.88 | | 8.8 |
| | | | | 3rd cycle: 120° C., 7 h | 1.0 | 3.71 | | 37 |
| | | | | 4th cycle: 120° C., 7 h | nd | 2.40 | | nd |

Compound 9 is 1-[3-(triethoxysilyl)propyl]-1,4,8,11-tetraazacyclotetradecane.

What is claimed is:

1. A compound of formula (I):

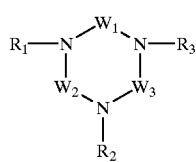

(I)

in which:

W₁, W₂ and W₃, which are identical or different, each represent, independently of one another, a divalent radical chosen from those represented by the general formula (A):

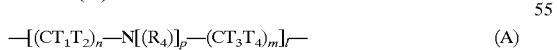

in which:

p represents an integer equal to 0 or to 1, l represents an integer equal to 1 or to 2, n and m, which are identical or different, each represent, independently of one another, an integer less than or equal to 3 and greater than or equal to 1, T₁, T₂, T₃ and T₄, which are identical or different, either each represent, independently of one another, a hydrogen atom, a linear or branched alkyl radical comprising from 1 to 15 carbon atoms or benzyl, [2-pyridyl)methyl], [3-pyridyl)methyl] or phenethyl or else CT₁T₂ and/or CT₃T₄ represent a divalent group —(C=O)—, R₁, R₂, R₃ and R₄ represent radical represented by the general formula (B):

R₅—Si(X₁)(X₂)(X₃)    (B)

in which:

X₁, X₂ and X₃, which are identical or different, each represent, independently of one another, a hydrogen atom, a halogen atom or an OR₆ radical, in which R₆ represents a hydrogen atom or an alkyl radical comprising from 1 to 4 carbon atoms, R₅ represents a divalent radical derived from a saturated or unsaturated aliphatic hydrocarbon chain comprising from 1 to 10 carbon atoms, in which chain are optionally inserted one or more structural links chosen from the arylene group or the —O—, —S—, —O—C(=O)—, —N(R₇)—C(=O)— or —N(R₇)— fragments, in which fragments R₇ represents a hydrogen atom, an aliphatic hydrocarbon radical comprising from 1 to 6 carbon atoms, a benzyl radical or a phenethyl radical, said chain being unsubstituted or substituted by one or more radicals chosen from halogen atoms, the hydroxyl group, alkyl radicals comprising from 1 to 4 carbon atoms or benzyl or phenethyl radicals.

2. A compound of formula (Ic), corresponding to the formula (I) as defined in claim 1 in which $W_1$ and $W_2$, which are identical or different, represent a divalent radical of formula ($A_2$), corresponding to the formula (A) in which p is equal to 1 and the sum n+m is equal to 2 or to 3, and $W_3$ represents a radical of formula ($A_1$), corresponding to the formula (A) in which p is equal to 0 and the sum n+m is equal to 2 or to 3.

3. The compound of formula (I) as defined in claim 1, in which the radical of formula (B) is selected from the group consisting of 3-silylpropyl, (4-silylphenyl)methyl, 3-(triethoxysilyl)propyl, 3-[[3-(triethoxysilyl)propyl]oxy]-2-hydroxypropyl, [4-[[[3-(triethoxysilyl)propyl]amino]methyl]phenyl]methyl, [4-(triethoxysilyl)phenyl]propyl, 3-oxo-3-[[3-(triethoxysilyl)propyl]oxy]propyl and 2-oxo-2-[[3-(triethoxysilyl)propyl]amino]ethyl radicals.

4. The compounds of formula (I) as defined in claim 1 with the following names:

- 1,4,8,11-tetrakis[3-(triethoxysilyl)propyl]-1,4,8,11-tetraazacyclotetradecane,
- 1,4,8,11-tetrakis[[4-(triethoxysilyl)phenyl]methyl]-1,4,8,11-tetraazacyclotetradecane,
- tetra[3-(triethoxysilyl)propyl]1,4,8,11-tetraazacyclotetradecane-1,4,8,11-tetrapropanoate,
- 1,4,8,11-tetrakis(3-silylpropyl)-1,4,8,11-tetraazacyclotetradecane,
- 1,4,8,11-tetrakis[(4-silylphenyl)methyl]-1,4,8,11-tetraazacyclotetradecane,
- $N_1,N_2,N_3,N_4$-tetrakis[3-(triethoxysilyl)propyl]-1,4,8,11-tetraazacyclotetradecane-1,4,8,11-tetraacetamide, or
- 4,11-bis[[4-(triethoxysilyl)phenyl]methyl]-1,4,8,11-tetraazacyclotetradecane-7,14-dione.

5. A polysiloxane gel (IV) incorporating polyazamacrocycles and metal complexes of these nitrogenous ligands, which is capable of being obtained from the action of a metal salt on the compound of formula (I) as defined in claim 1, resulting in the formation of an organometallic complex of said metal with said compound of formula (I), followed by the hydrolysis of said organometallic complex.

6. A compound of formula (Ia), corresponding to the formula (I) as defined in claim 1 in which $W_1$, $W_2$ and $W_3$, which are identical or different, represent a radical of formula ($A_1$), corresponding to the formula (A) in which p is equal to 0 and the sum n+m is equal to 2 or to 3.

7. A compound of formula ($Ia_1$), corresponding to the formula (Ia) as defined in claim 2, in which l is equal to 1 and either $W_1$, $W_2$ and $W_3$ each represent the divalent radical —$CH_2$—$CH_2$—$CH_2$— or else any one of the three groups $W_1$, $W_2$ or $W_3$ represents the divalent radical —$CH_2$—$CH_2$—$CH_2$— and each of the other two groups represents the divalent radical —$CH_2$—$CH_2$—.

8. A compound of formula (Ib), corresponding to the formula (I) as defined in claim 1 in which $W_1$ represents a divalent radical of formula ($A_2$), corresponding to the formula (A) in which p is equal to 1 and the sum n+m is equal to 2 or to 3, and $W_2$ and $W_3$, which are identical or different, represent a radical of formula ($A_1$), corresponding to the formula (A) in which p is equal to 0 and the sum n+m is equal to 2 or to 3.

9. A compound of formula ($Ib_1$), corresponding to the formula of (Ib) in claim 3, in which l is equal to 1 and either any one of the three groups $W_1$, $W_2$, or $W_3$ represents the radical —$CH_2$—$CH_2$—$CH_2$—$N(R_4)$—$CH_2$—$CH_2$—, either one of the two remaining groups represents the radical —$CH_2$—$CH_2$— and the final group represents the racial —$CH_2$—$CH_2$—$CH_2$— or else any one of the three groups $W_1$, $W_2$ or $W_3$ represents the radical —$CH_2$—$CH_2$—$CH_2$—$N(R_4)$—$CH_2$—$CH_2$—$CH_2$— and the other two remaining groups each represent the radical —$CH_2$—$CH_2$—$CH_2$—.

10. A polysiloxane gel (III) incorporating polyazamacrocycles and metal complexes of these nitrogenous ligands, which is capable of being obtained from the hydrolysis of the compound of formula (I) as defined in claim 1, resulting in the formation of a polysiloxane gel incorporating non-metallated polyazamacrocycle units (III'), followed by the action of a metal salt on said gel (III').

11. A method of purifying a liquid from cationic impurities, wherein said liquid is brought in contact with a polysiloxane gel incorporating non-metallated polyazamacrocycle units (III') as defined in claim 10.

12. A process for the preparation of the polysiloxane gel (III), wherein the compound of formula (I) as defined in claim 1 is subjected to hydrolysis, resulting in the formation of a polysiloxane gel incorporating non-metallated polyazamacrocycle units (III'), and then wherein said gel (III') is reacted with a metal salt.

13. A process for the preparation of the polysiloxane gel (IV), wherein the compound of formula (I) as defined in claim 1 is reacted with a metal salt, resulting in the formation of an organometallic complex of said metal with said compound of formula (I), and then wherein said organometallic complex is subjected to hydrolysis.

14. An alternative form of the process as defined in claim 12 or 13, in which the metal cation involved in the composition of the polysiloxane gel (III) or (IV) is selected from the cations consisting of $Cu^{2+}$ and $Co^{2+}$.

15. A method of separation of a predetermined gas from a mixture of gases wherein said mixture of gases is brought into contact with one of the metallated hybrid gels (III) as defined in claim 12, under conditions which make possible the absorption of said gas to be separated, followed by a phase of desorption of said gas attached to said gel and by a phase of recovery of said desorbed gas.

16. A method as defined in claim 15, wherein the mixture of gases is air and the gas to be separated is oxygen.

17. A method of separation of a predetermined gas from a mixture of gases wherein said mixture of gases is brought into contact with one of the metallated hybrid gels (IV) as defined in claim 13, under conditions which make possible the absorption of said gas to be separated, followed by a phase of desorption of said gas attached to said gel and by a phase of recovery of said desorbed gas.

18. A method as defined in claim 17, wherein the mixture of gases is air and the gas to be separated is oxygen.

* * * * *